Feb. 26, 1952 E. P. DERING Plant Pat. 1,076
ROSE PLANT
Filed Dec. 8, 1950
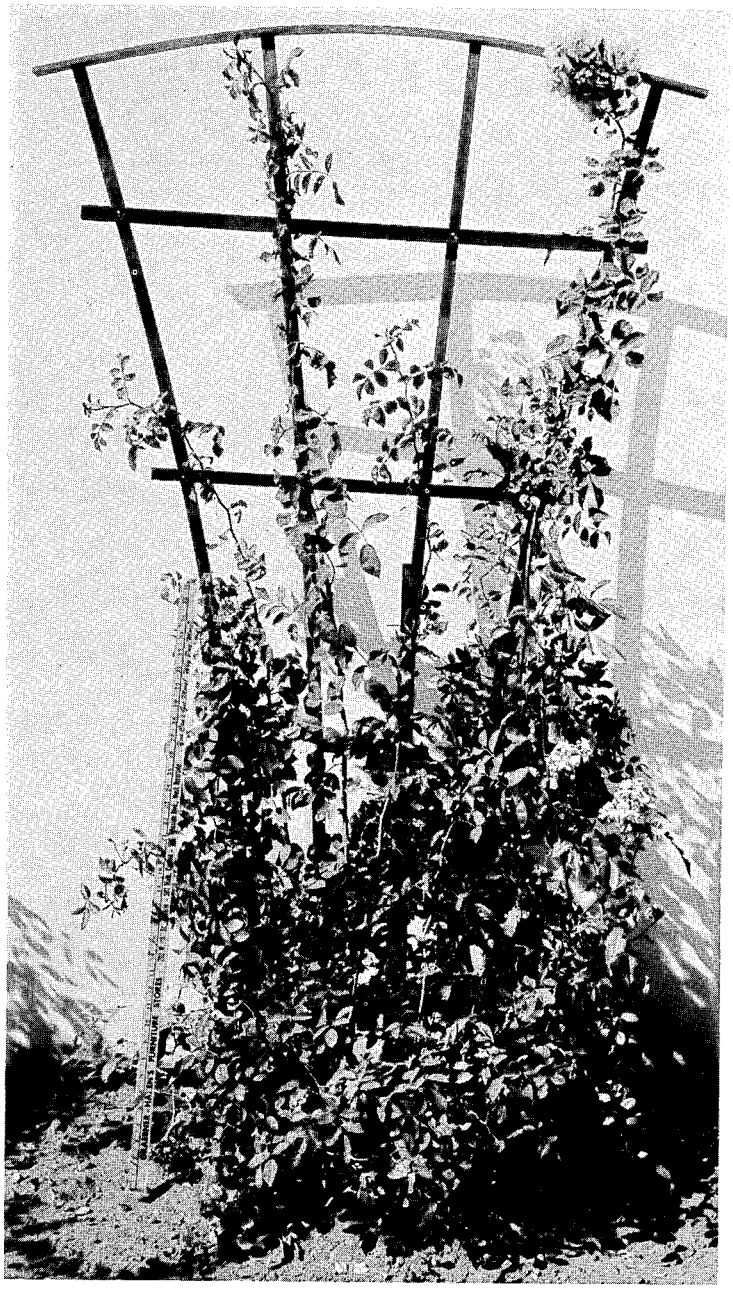
Inventor.
E. P. Dering
By: Robb & Robb
Attorneys.

Patented Feb. 26, 1952

Plant Pat. 1,076

UNITED STATES PATENT OFFICE 1,076

ROSE PLANT

Eldon P. Dering, Scappoose, Oreg., assignor to Armstrong Nurseries, Inc., Ontario, Calif., a corporation of California Application December 8, 1950, Serial No. 199,779

1 Claim. (Cl. 47—61)

The present invention relates to a new and distinct variety of rose plant, originating in a nursery row on my property as a cultivated bud sport of the variety "Pinkie" (Plant Patent No. 712), and principally distinguished therefrom by its climbing habit of growth.

The parent variety is a bush rose of the polyantha class and is particularly notable for its relatively loose and graceful habit of growth, large and broad trusses of bloom, relatively large individual flowers of fast, light pink color, perfection of form of the buds and half-open flowers, and by its free-blooming trait.

The new variety herein has substantially the same general form, color and habit of flower as its parent, but is primarily distinct therefrom by its more vigorous growing habit as evidenced by its strong canes which attain a height of five to six feet or more as compared with the usual height of fifteen to twenty inches attained by the bush form of the variety "Pinkie" when grown under comparable conditions.

In addition, the new variety produces many more flowers than can usually be found at any one time on the parent bush variety, and its flowering habit is much more nearly continuous during the growing season than that of any other climber of which I am aware.

Asexual reproduction of the new variety by budding at Scappoose, Oregon, shows that the foregoing characteristics come true to form and are established and transmitted through succeeding propagations.

The accompanying drawing shows a specimen plant of the new variety in comparison with a conventional three-foot measuring scale or yardstick beside the plant, by way of convenient illustration of the relative height of the long canes which are typical of this new climbing sport.

The following is a detailed description of the new variety, with color terminology in accordance with Robert F. Wilson's Horticultural Colour Chart except where otherwise noted as Ridgway's Color Standards and Nomenclature:

Type: Climbing sport; for garden decoration.
Class: Climbing polyantha.
Breeding: Bud sport of bush rose "Pinkie."
Propagation: Holds its distinguishing characteristics by budding.

*Flower*

Locality where grown: Ontario, California.
Flowers borne: Several to stem in rounded cluster; on normal strength, medium length stems for a polyantha.

Quantity of bloom: Very abundant; outdoors.
Continuity: Nearly continuous during the growing season; the only break in the continuous flowering habit is when new growth is being put on to form the next mass of flower buds. The flowers are produced on sucker growth which arise from the base of the plant as well as from secondary branching from the main canes.
Fragrance: Slight; musk to spicy.
Bud:
*Peduncle.*—Short; slender; erect; moderately rough; numerous gland-tipped cilia and numerous hairs. Color—Biscay Green, Plate XVII (Ridgway) to near Sulphine Yellow, Plate IV (Ridgway) on side exposed to the sun.
*Before calyx breaks.*—Size—medium for polyantha. Form—short; ovoid; with foliaceous appendages, thin pubescence, gland-tipped cilia and glandular bloom on the surface of the bud; with slender foliaceous parts extending beyond the tip of the bud equal to one-fourth or more of its length.
*As calyx breaks.*—Color—Camellia Rose, Plate 622, page 148.
*Sepals.*—Inner surface—with fine, woolly tomentum; covered margins have only woolly tomentum, while uncovered margins have woolly tomentum and stipitate glands.
*As first petal opens.*—Size—average for polyantha. Form — long, pointed to urn-shaped. Color—outside: Camellia Rose, Plate 622/1, page 148; inside: near Spinel Pink, Plate 0625/2, page 184.
*Opening.*—Opens up well. Is not prevented from opening by cold, hot, wet or dry weather.
Bloom:
*Size, when fully open.*—Average for polyantha; 1¾ inches to 2¾ inches.
*Petalage.*—Double (but the stamens not hidden) 14 to 20 petals, plus 1 to 3 petaloids; arranged regularly.
*Form.*—High centered at first; becoming open to cupped; petals being at first cupped with tips reflexed and rolled outward; becoming later at maturity flat cupped with tips rolled outward.
Petals:
*Texture.*—Thick; with inside satiny and outside slightly shiny.
*Shape.*—Outside—cuneate with apex flat. Intermediate—cuneate with apex flat. Inside—narrowly cuneate with apex flat.

*Color.*—Colors may be modified by being dotted or blotched with other colors in foggy weather.

This description of a newly opened flower was made from a rose grown outdoors in the month of June, 1950, at Ontario, California:

*Color.*—*Outside petal*—outside surface: near Phlox Pink, Plate 625/1, page 77; inside surface: near Neyron Rose, Plate 623/2, page 76. *Intermediate petal*—outside surface: near Phlox Pink, Plate 625/1, page 77; inside surface: near Neyron Rose, Plate 623/1, page 76. *Inner petal*—outside surface: near Phlox Pink, Plate 625/1, page 77; inside surface: near Neyron Rose, Plate 623/1, page 76.

This description was made from a rose that was open for three days outdoors in the month of June, 1950, at Ontario, California:

*Color.*—*Outside petal*—outside surface: near Phlox Pink, Plate 625/3, page 77; inside surface: near Rose Pink, Plate 427/1, page 126, dotted with Rose Opal, Plate 022/1, page 110, when affected by fog or dew. *Inside petal*—outside surface: near Phlox Pink, Plate 625/2, page 77; inside surface: near Neyron Rose, Plate 623/2, page 76.

*General color effect.*—Newly opened flower—near Neyron Rose, Plate 623/1, page 76. Three days open—near Neyron Rose, Plate 623/3, page 76, dotted with Rose Opal, Plate 022/1, page 110, on outside petals as a result of fog.

*Behavior.*—Drop off cleanly; fading to lighter color; affected by hot, dry weather by fading to lighter color. In foggy or wet weather the outside petals become dotted with a deeper color.

*Flower longevity.*—On bush in garden—3 to 4 days in June. Cut roses grown outdoors kept at living room temperatures—2 to 3 days in June.

*Reproductive organs*

Stamens: Average number; arranged regularly about pistils, a few mixed with petaloids.

Filaments: Medium length to long; from 1½ mm. to 6 mm. long. Color—near Canary Yellow, Plate 2/2, page 2. Most with anthers.

Anthers: Medium size to large for polyantha; all open at once approximately. Color—in newly opened flower near Lemon, Plate 4/2, page 4, to Buttercup Yellow, Plate 5/2, page 5, at margin.

Pollen: Moderate. Color—near Buttercup Yellow, Plate 5/2, page 5.

Pistils: Many for polyantha; approximately 20 in number.

Styles: Even; length 2 mm. to 3 mm.; average caliper; bunched. Color—near Crimson, Plate 22/2, page 22, to near Chartreuse Green, Plate 663/3, page 90.

Stigma: Color—clear greyish white, more or less translucent.

Ovaries: All enclosed in calyx.

Hips: Ovoid; moderately smooth; walls thick, fleshy. Color—near Yellow Ocher, Plate XV (Ridgway) on side exposed to sun, to near Courge Green, Plate XVII (Ridgway) on the side not exposed to the sun.

Sepals: Falling soon; moderately long; recurved. Color (sepals from newly opened flower)—inside: near Deep Chrysolite Green, Plate XXXI (Ridgway) blushed with Cacao Brown, Plate XXVIII (Ridgway); outside: near Asphodel Green, Plate XLI (Ridgway), blotched with Cacao Brown, Plate XXVIII (Ridgway), particularly at margin.

Seeds: Few; large for polyantha; 2 to 3 in number per hip.

*Plant*

Foliage:

*Leaves.*—Compound of three to seven leaflets; normal to abundant; medium size; moderately thin, soft and glossy.

*Leaflets.*—Shape—ovoid to lanceolate with apex acute; base—obtuse; margin—simply serrate.

*Color.*—*Mature*—upper surface: near Bice Green, Plate XVII (Ridgway); under surface: near Light Cress Green, Plate XXXI (Ridgway). *Young*—upper surface: near Cress Green, Plate XXXI (Ridgway) with Brick Red, Plate XIII (Ridgway) shading, particularly at the border; under surface: near Mignonette Green, Plate XXXI (Ridgway) with Brick Red, Plate XIII (Ridgway) shading, particularly at the border of leaflet.

*Rachis.*—Heavy. Upper side: grooved, with few stipitate glands on edges; under side: moderately prickly.

*Stipules.*—Medium length to long; medium width to wide, with medium-length to long points turning out at an angle of more than 45°.

*Disease.*—Resistant to mildew.

Growth:

*Habit.*—Climbing; much branched.

*Growth.*—Free.

*Canes.*—Medium caliper.

*Main stems.*—Color—near Calla Green, Plate V (Ridgway). *Large prickles*—few; long; hooked slightly downward; with long, narrow base. Color—near Hazel, Plate XIV (Ridgway). *Small prickles and hairs*—none.

*Branches.*—Color—near Courge Green, Plate XVII (Ridgway). *Large prickles*—none. *Small prickles and hairs*—none.

*New shoots.*—Color—on smaller new shoots, near Parrot Green, Plate VI (Ridgway) with Pompeian Red, Plate XIII (Ridgway) shadings on side exposed to sun. On strong new shoots, near Morocco Red, Plate I (Ridgway). *Large prickles*—none. *Small prickles and hairs*—none.

I claim:

A new and distinct variety of rose plant of the climbing polyantha class, characterized as to novelty by its general similarity to its parent "Pinkie" (Pl. Pat. No. 712) in form, color and habit of flower, but distinguished therefrom by its more vigorous growing habit as evidenced by its strong, climbing canes, by its production of many more flowers than can usually be found at any one time on its parent bush variety, and by its more nearly continuous flowering habit during the growing season than that of other climbers, substantially as shown and described herein.

ELDON P. DERING.

No references cited.